United States Patent [19]

van Lintel

[11] Patent Number: 5,224,843

[45] Date of Patent: Jul. 6, 1993

[54] TWO VALVE MICROPUMP WITH IMPROVED OUTLET

[75] Inventor: Harald T. G. van Lintel, Enschede, Netherlands

[73] Assignee: Westonbridge International Ltd., Dublin, Ireland

[21] Appl. No.: 651,404

[22] PCT Filed: Jun. 12, 1990

[86] PCT No.: PCT/CH90/00145

§ 371 Date: Feb. 13, 1991

§ 102(e) Date: Feb. 13, 1991

[87] PCT Pub. No.: WO90/15929

PCT Pub. Date: Dec. 27, 1990

[30] Foreign Application Priority Data

Jun. 14, 1989 [CH] Switzerland ............ 02241/89
Aug. 7, 1989 [FR] France ............ 89 10699

[51] Int. Cl.⁵ ............ F04B 17/00; F16K 15/14
[52] U.S. Cl. ............ 417/413 A; 417/322; 417/413 B; 137/859
[58] Field of Search ............ 417/322, 410, 413; 137/855, 859

[56] References Cited

U.S. PATENT DOCUMENTS 4,265,600  5/1981  Mandroian .
4,265,601  5/1981  Mandroian .
4,911,616  3/1990  Laumann, Jr. ............ 417/413

FOREIGN PATENT DOCUMENTS 134614   3/1985  European Pat. Off. ............ 417/413
2639992  3/1978  Fed. Rep. of Germany .
2127774  10/1972 France .
2077367  12/1981 United Kingdom .

OTHER PUBLICATIONS

Petersen, "Silicon as a Mechanical Material", Proceeding of the IEEE, vol. 70, No. 5, May 1982, p. 420.
Van Lintel, "A Piezoelectric Micropump Based on Micromachining of Silicon, Sensors and Actuators", vol. 15, No. 2, Oct. 1988, pp. 153-167.
International Search Report.

*Primary Examiner*—Richard A. Bertsch
*Assistant Examiner*—Roland McAndrews
*Attorney, Agent, or Firm*—Pollock, Vande Sande & Priddy

[57] ABSTRACT

Pumping takes place within the micro-pump as a result of the deformation of a plate (12) using a piezo-electric pad (13). The deformation produces a variation in volume within a pumping chamber (15) defined inside a plate (11) which is made of a material which can be machined using photolithographic processes. The pump outlet (3) is blocked off, selectively, by a membraned check-valve (18) which is in direct communication with another check-valve (16) via the pumping chamber. The check-valve (16) selectively enables the pumping chamber to communicate with the pump inlet (2). The outlet valve membrane (18) has a layer of oxide (17) providing a pretension on closing. The check-valve thus has a regulatory effect on the pump operation, making the flow almost independent of the outlet (3) pressure. Application: injection of exact doses of medication.

20 Claims, 7 Drawing Sheets

TWO VALVE MICROPUMP WITH IMPROVED OUTLET

TECHNICAL FIELD

The present invention relates to micropumps in which at least part of the pump mechanism is made by machining a silicon wafer using photolithographic technology.

Pumps of this type can be used notably for the in situ administration of medicaments whereby miniaturization of the pump enables the patient to wear it on his person or possibly to have a pump directly implanted in his body. In addition, using pumps of this type, small quantities of liquid to be injected can be accurately metered.

BACKGROUND OF THE INVENTION

In an article entitled "A piezoelectric micropump based on micromachining of silicon" which appeared in "Sensors and Actuators" No. 15 (1988), pages 153 to 167, H. van Lintel et al describe two embodiments of a micropump each comprising a stack of three wafers, i.e. a wafer of machined silicon arranged between two wafers of glass.

The silicon wafer defines a pumping chamber with one of the glass wafers, it being possible for the part coinciding with this chamber to be deformed by a driving element, in the present case a piezoelectric crystal. The latter comprises electrodes which, when connected to a source of alternative potential, cause deformation of the crystal and thus of the glass wafer, the latter in turn causing variation in the volume of the pump chamber.

The pump chamber is connected on one side and on the other side respectively to check valves machined from silicon the seat of which is composed of the other glass wafer.

Study of the mode of operation of the pump according to the first embodiment (FIG. 1a) described in the above mentioned article shows that the fluid output delivered by this pump depends greatly on the outlet pressure over the entire operating range. It was found that this relationship between output and pressure is virtually linear, the output falling as pressure rises.

In other words, a pump of this type cannot be used for the above mentioned medical applications in which, in contrast, the output from the pump outlet must be independent of the pressure, at least in the normal operating range of the pump.

For this reason the authors propose in this same article (second embodiment shown in FIG. 1b) adding a regulating valve to the above described assembly disposed between the second valve downstream from the pumping chamber and the pump outlet. This valve isolates the pump from the outlet when it is closed.

Moreover, since the regulating valve has a certain degree of mechanical pretension towards closure, the outlet pressure is only able to open the valve after reaching a certain value. As a result, a form of independence of output in relation to outlet pressure develops in the useful operating range of the pump, i.e. when the regulating valve is not kept open by the outlet pressure.

Thus, although this second design gives a favourable output pressure diagram, it should nevertheless be noted that a pump manufactured in this manner still has disadvantages.

The regulating valve increases the pump size since it must be situated within the silicon wafer and thus takes up additional surface area. It also increases the cost price of the pump.

It should also be noted that the regulating valve increases the complexity of the pump and thus the risk of incorrect functioning or manufacturing error.

SUMMARY OF THE INVENTION

It is an object of the invention to provide a micropump of the type set out above which avoids the disadvantages of the pumps described in the above mentioned article whilst presenting good output characteristics in relation to the outlet pressure over the useful operating range of the pump.

It is thus an object of the invention to provide a micropump having a first wafer of a material capable of being machined using photolithographic technology in such a way as to define with at least one second support wafer bonded face to face with the first wafer a pump chamber, a first valve of the check-valve type through which said pump chamber is able to communicate selectively with one pump inlet and a second valve of the membrane type through which said pump chamber can communicate selectively with one outlet of the pump, means being provided to cause a periodic variation in the volume of said pump chamber, characterized in that said outlet communicates directly with an isolated volume of said pump chamber by means of said second valve and situated on the same side of this valve as the channel through which this valve communicates with the pump chamber in such a way that both the pressures prevailing in this pump chamber and this volume act in the direction of opening on said second valve and in that said second valve is in open communications with said first valve via said pump chamber in such a way that, during the outlet phase of the pump, this chamber communicates directly with said outlet through said second valve in the open position.

By virtue of these characteristics, said second valve not only regulates output in such a way as to render the latter virtually independent of the pressure in the pump outlet over its entire normal operating range, but it also acts as the element closing the pump chamber during the inlet phase of the pump.

BRIEF DESCRIPTION OF THE DRAWINGS

Other characteristics and advantages of the invention are better illustrated by the following description of several embodiments of the micropump according to the invention, with reference to the accompanying drawings, in which.

DETAILED DESCRIPTION OF THE INVENTION

Figure 1:
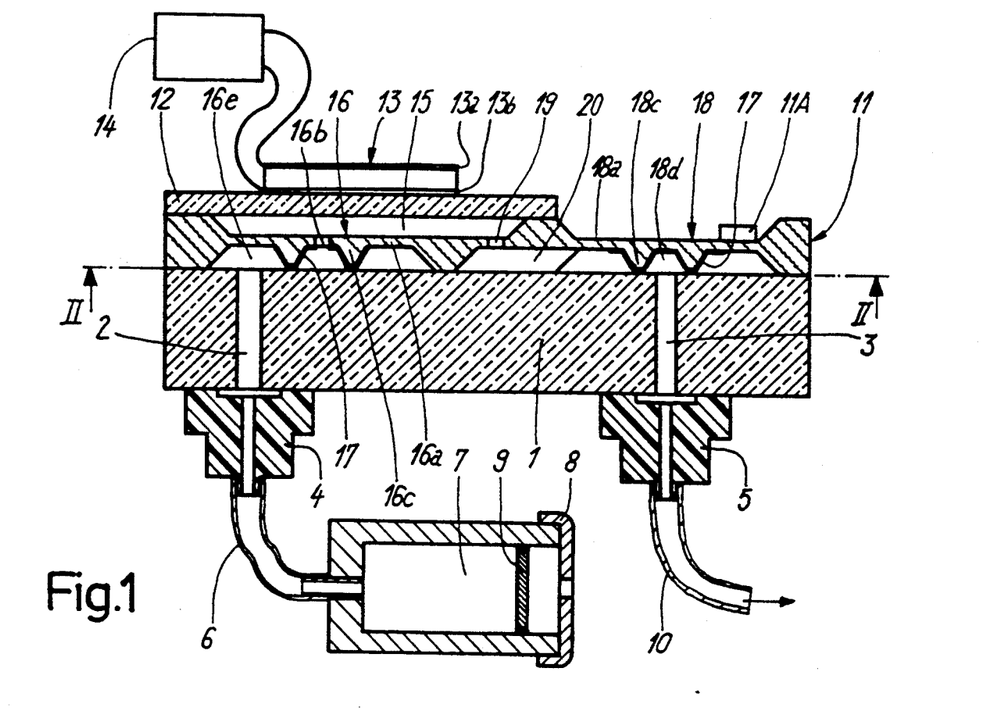
FIG. 1 is a diagrammatic sectional view of a micropump according to the invention.
Figure 2:
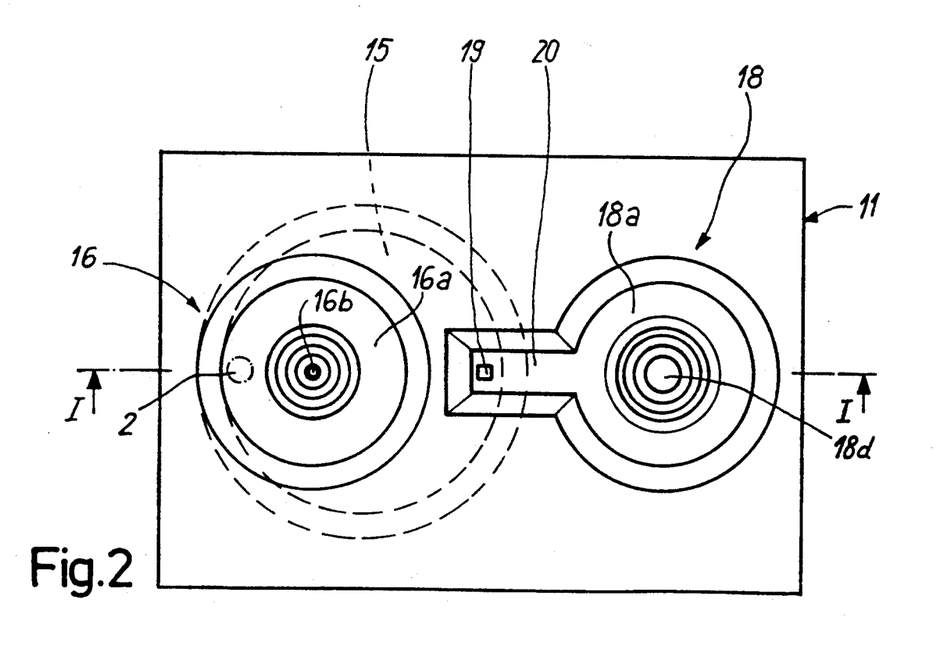
FIG. 2 shows a plan view of the intermediate wafer of the pump shown in FIG. 1.

Reference will first be made to FIGS. 1 and 2 which show a first embodiment of the micropump according to the invention.

It should be noted that the thicknesses of the various wafers comprising the micropump have been greatly exaggerated in the drawings in the interest of clarity.

The micropump of FIGS. 1 and 2 has a base wafer 1 of, for example, glass, which is pierced by two channels 2 and 3 forming the inlet channel and the outlet channel of the pump respectively. These channels 2 and 3 communicate with connectors 4 and 5 respectively.

The connector 4 is connected to a tube 6 which in turn is connected to a reservoir 7 containing the liquid to be pumped. The reservoir is closed by a pierced cap, a movable piston isolating the working volume of the reservoir 7 from the outside. This reservoir can, for example, contain a medicament if the pump is used to inject a precise dose of this medicament into the human body. In this application the micropump can be worn on the body of the patient or implanted therein.

The outlet connector 5 may be connected to an injection needle (not shown) joined thereto by a tube 10.

Use of the micropump of the invention in this manner is particularly suitable for treating certain forms of cancer with peptides where medication should preferably be in the form of accurate and repeated doses of small amounts of the medicament at regular intervals. Another potential application could be for the treatment of diabetics who need regular low doses of a medicament in the course of the day, the dose being determined for example by means known per se, measuring the blood sugar level and automatically instructing the pump to inject a suitable dose of insulin.

A wafer 11 of silicon or other material capable of being machined using photolithographic etching technology is bonded to the glass wafer 1. Above this silicon wafer is a glass closure wafer 12, the thickness of which is such that it can be deformed by a control element 13 which, in the application of the invention described herein, is a piezoelectric disc provided with electrodes 13a and 13b connected to an alternative voltage generator 14. This disc may be that manufactured by Philips under the reference number PXE-52 and may be bonded to the wafer 12 using a suitable adhesive.

For purposes of example, the intermediate silicon wafer 11 can have a <100> crystalline orientation so as to render it suitable for etching and to give it the requisite strength. The wafers 1 and 12 are preferably carefully polished.

The wafers 11 and 12 together define first of all a pumping chamber 15 (see also FIG. 2) for example circular in shape, this chamber being situated below an area of the wafer 12 which can be flexed by the control element 13.

A first valve 16 of the check-valve type machined out of the silicon wafer 11 is interposed between the inlet channel 2 and the pump chamber 15. This valve is located under the pump chamber and comprises a membrane 16a substantially circular in shape and pierced in its centre by an opening 16b which is square in the embodiment shown. On the side of the channel 2, the valve 16 has an annular rib 16c which is substantially triangular in section. This rib 16c surrounds the opening 16b and is covered by a fine oxide layer 17 also obtained using photolithographic technology. This oxide layer induces an extra thickness which subjects the membrane 16a to a certain degree of bias or pretension when the top of the rib 16c bears against the glass wafer 1, the latter thus acting as seat for the valve 16.

The outlet channel 3 of the pump communicates with the pump chamber 15 via a valve 18, the design of which is identical to that of the valve 16 except for the thickness of the layer 17 compared to that of the valve 16, the bias imposed by this oxide layer 17 can differ from that used for the valve 16. Furthermore, FIG. 1 shows that this valve does not have a central opening similar to the opening 16b of the valve 16.

It will be noted that the pump chamber communicates with the valve 18 via an opening 19 and a passage 20, both machined in the silicon wafer 11.

The valve 18 thus comprises a membrane 18a partially covered and an annular rib 18c covered by an oxide layer 17 and define above the channel 3 a volume 18d in which the outlet pressure prevails. The oxide layer of membrane 18a creates shearing forces in it, which induce the membrane to bulge out (oxide layer is on the convex side of the membrane). This causes an additional pretension towards closure of the valve, with respect to the pretension induced by the oxide layer covering the rib 18c. When the valve 18 is opened, volume 18d communicates directly with the inlet valve 16 through the pump chamber 15 with the result that a minimum of flow resistance is imposed on the fluid driven out of the pump during the output phase. Moreover, when the valve 18 is closed, the outlet pressure only acts on a small area of the membrane 18a compared to the substantially larger area on which the pressure prevailing in the pump chamber is able to act. This results in regulation of the outlet output which becomes virtually independent of the outlet pressure (see FIG. 13), this effect being produced by the pretension provided by the oxide layer 17.

By way of example, the thickness of the wafers 1, 11 and 12 may be about 1 mm, 0.3 mm and 0.2 mm respectively for a surface area of the wafers of the order of 15 by 20 mm.

The wafers may also be fixed to one another using various conventional bonding technology such as adhesion or, for example, the technology known as anodic bonding.

Figure 3:
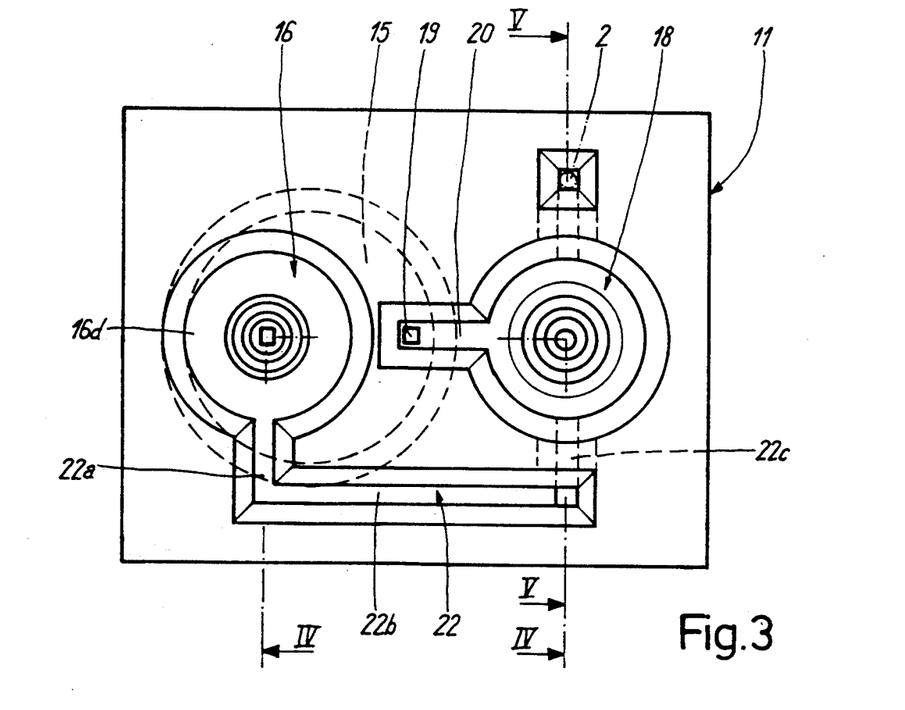
FIG. 3 is a view showing the lower face of the intermediate wafer of a micropump designed according to a second embodiment of the invention, the view being taken along the line III—III of FIG. 4.
Figure 4:
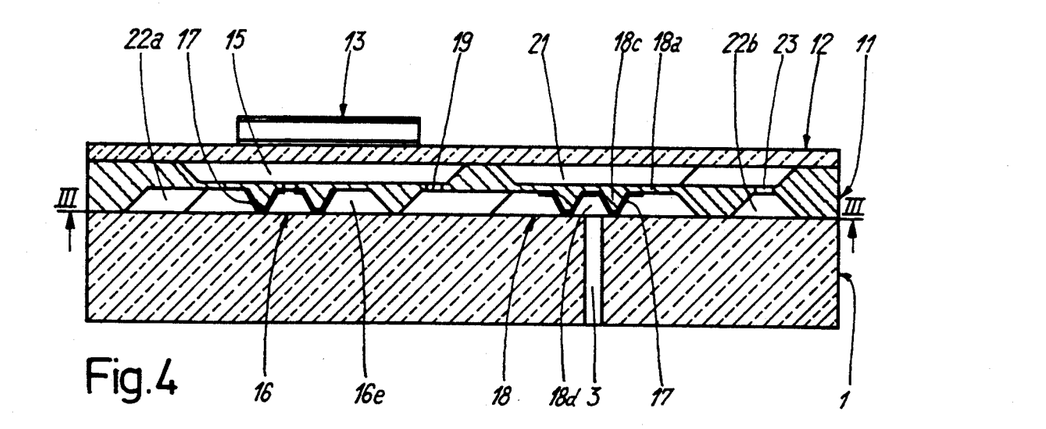
FIGS. 4 and 5 are sectional views taken along the lines IV—IV and V—V respectively of FIG. 3.
Figure 5:
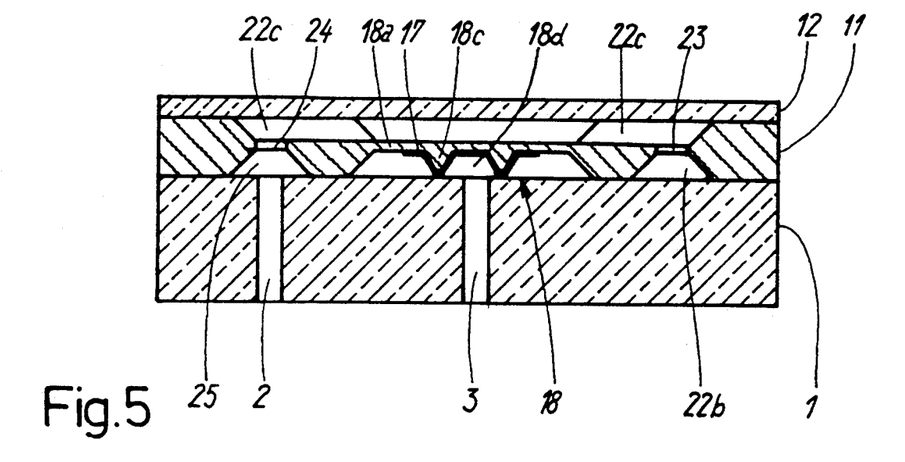

FIGS. 3 to 5 show a second embodiment of the micropump of the invention which is substantially identical in design to the micropump shown in FIGS. 1 and 2. The identical elements consequently bear the same reference numerals given earlier. However it differs in that the annular chamber 16e (FIG. 4) surrounding the annular rib 16c of the inlet valve 16 is not only connected to the inlet channel 2, but also to a compensation chamber 21 defined in the wafer 11 above the valve 18 and closed by the closure wafer 12, this latter in this case covering the entire surface of the pump. This connection is provided by the intermediary of a communicating channel 22 machined in the silicon and composed of three branches 22a, 22b and 22c disposed at right angles in the wafer 11. It should be noted that the branch 22c of this channel is not at the same level as the two other branches 22a and 22b, the branches 22b and 22c communicating with one another via a communicating opening 23 provided in the wafer 11. In addition, the branch 22c (FIG. 5) communicates with the inlet channel 2 via a communicating opening 24 which connects this branch to a small cavity 25 provided in the silicon wafer 11 just above the inlet channel 2.

The channel 22 is designed to provide a communication between the channel 2 of the pump and the chamber 21 provided above the membrane 18a of the outlet valve 18 in such a way as to keep this closed if there is overpressure at the entrance to the pump. This arrangement serves to guard against overpressure.

Figure 6:
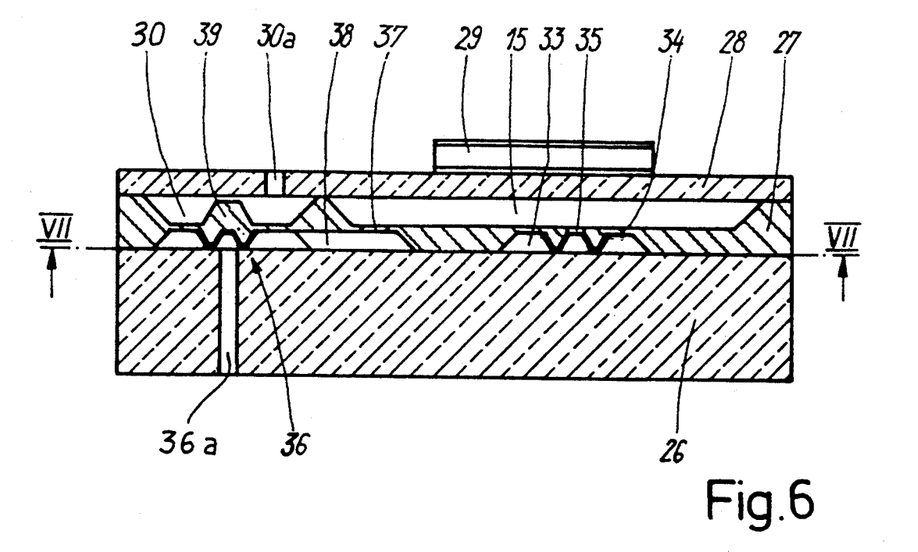
FIG. 6 is a sectional view of a micropump constructed according to a third embodiment of the invention.
Figure 7:
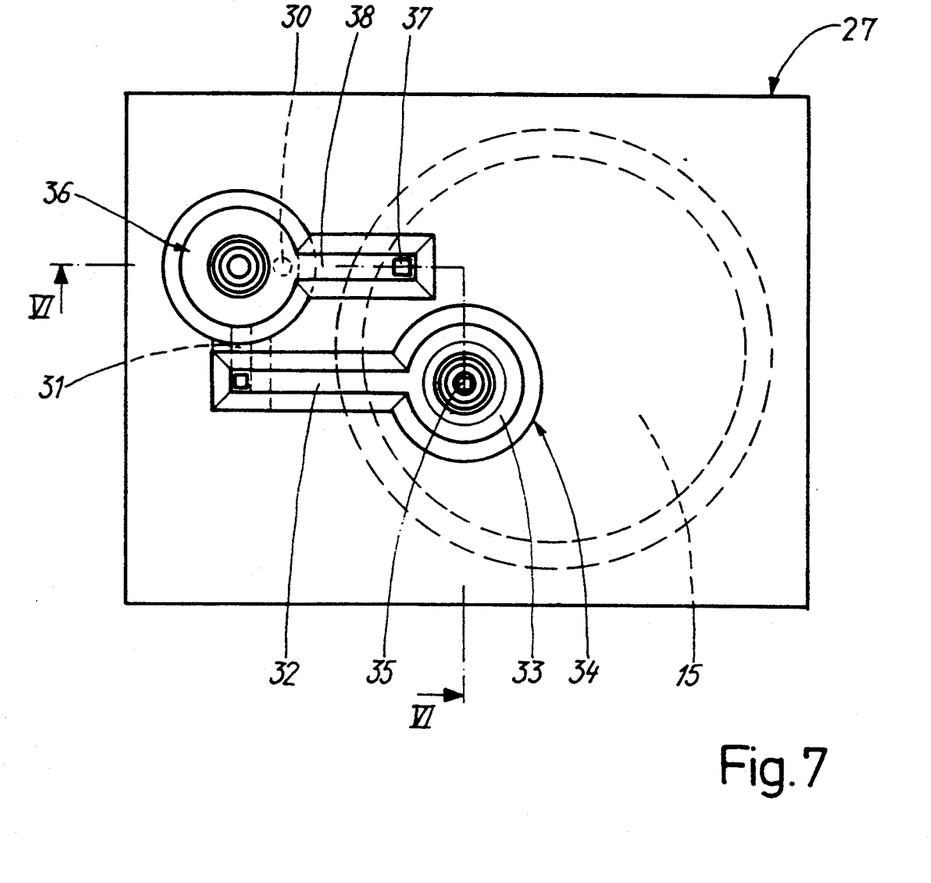
FIG. 7 is a view of the lower face of the intermediate wafer of the pump shown in FIG. 6, this view being taken along the line VII—VII of FIG. 6.

FIGS. 6 and 7 to which reference will now be made represent a third embodiment of the micropump of the invention. In this case, the above described design principle remains the same except that the pump chamber 15 is disposed asymmetrically in respect of the inlet and outlet valves.

This pump is also composed of three wafers, namely a support wafer 26, of, for example, glass, a wafer of 27 of, for example silicon or other suitable material, and a closing wafer 28 of, for example, flexible glass, located in a zone above the pump chamber 15 with the aid of a piezoelectric disc 29 or other suitable control element.

The pump chamber 15 is defined by the wafer 27 and the wafer 28, these two wafers also defining an inlet chamber 30 (shown only on FIG. 6) into which opens an inlet opening 30a which is provided in the wafer 28.

The chamber 30 communicates with a channel 31 (shown only in FIG. 7) located in the upper part of the wafer 27 and this channel 31 communicates with a second channel 32 provided in the wafer 27 on the side of the wafer 26. The channel 32 opens into an annular chamber 33 of an inlet valve 34 of identical design to that of the valve 16 previously described. This inlet valve communicates with the chamber 15 through a central opening 35.

The chamber 15 also communicates with an outlet valve 36 via an opening 37 and a channel 38 both provided in the wafer 27. In addition, the outlet valve 36 which is designed to close the outlet opening 36a (FIG. 6) is designed in the same way as the outlet valve of the preceding embodiments except that it has a projection 39 on the side of its membrane opposite the closing rib of the valve. This projection 39 which is at the center of the membrane is designed to limit the amplitude of movement thereof thanks to the effect of the stop which it can exert on the wafer 28 in the event that the outlet pressure exceeds a predetermined permissible value.

In the embodiment that has just been described the inlet opening 30a opens into the chamber 30 which is located above the outlet valve 36 and thus serves as compensation chamber similar to the chamber 21 of the preceding embodiment. This design consequently also provides a protection against overpressure.

Figure 8:
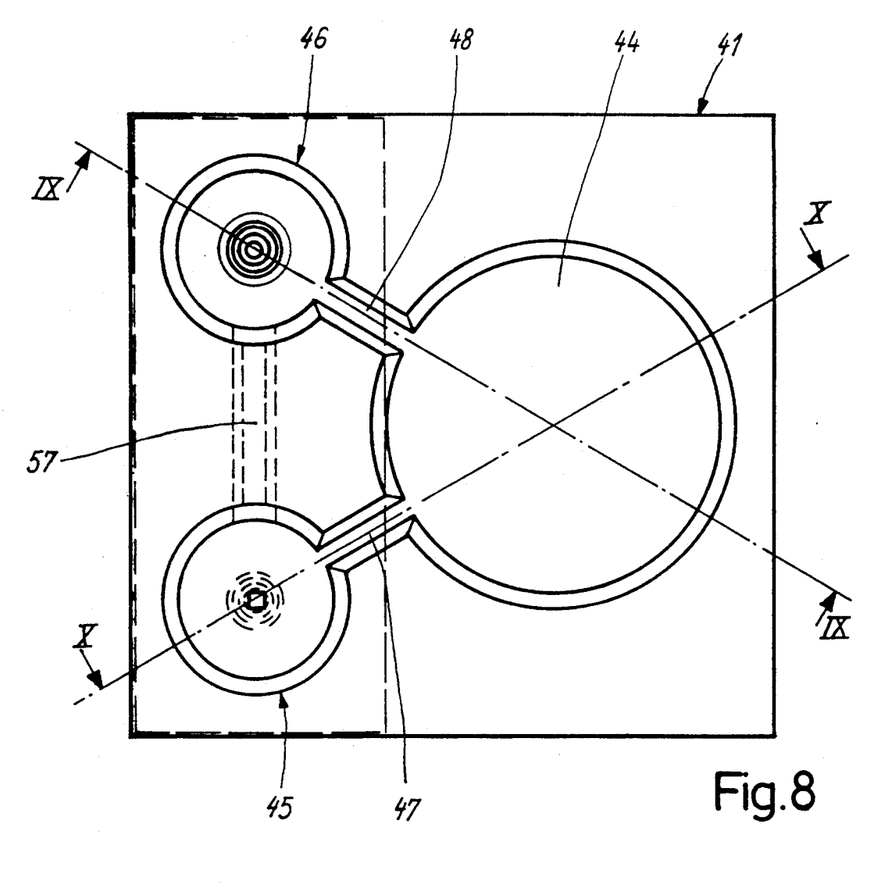
FIG. 8 is a view of the lower face of an intermediate wafer of a micropump constructed according to a fourth embodiment of the invention.
Figure 9:
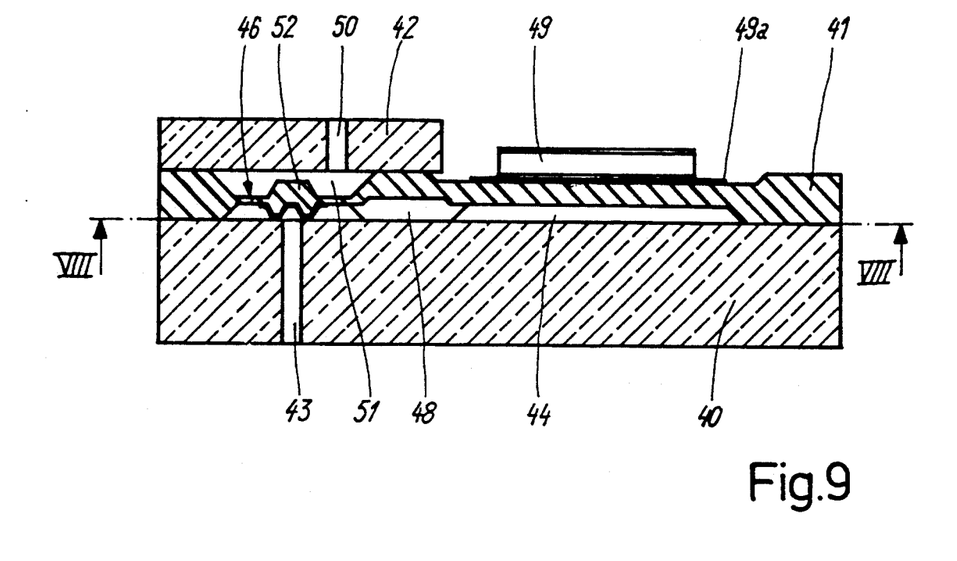
FIGS. 9 and 10 are sectional views taken along the lines IX—IX and X—X respectively of FIG. 8.
Figure 10:
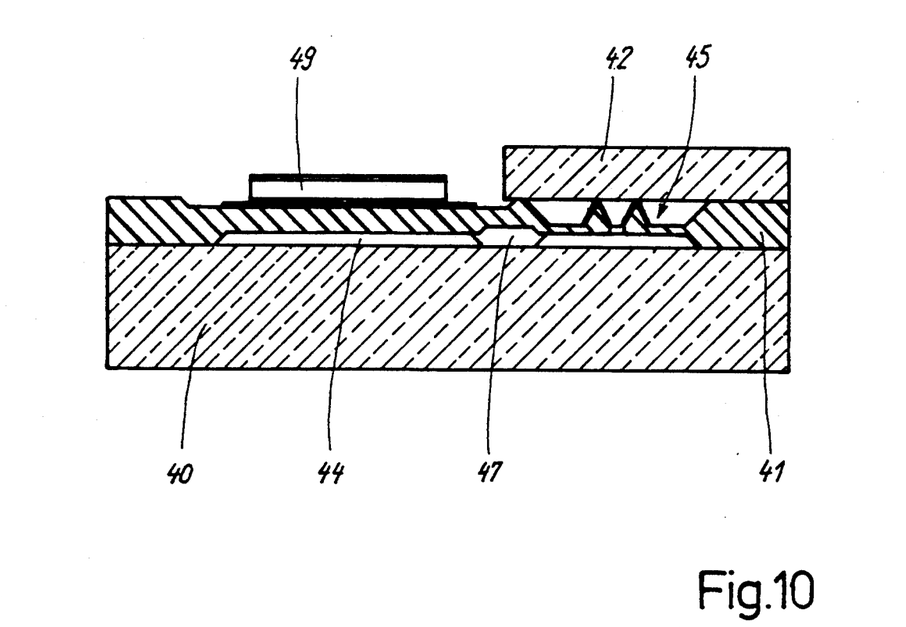

Reference will now be made to FIGS. 8 to 10 which represent a fourth embodiment of the invention.

In this case the micropump also has three wafers 40, 41 and 42. The wafer 40 is made for example of glass and has an outlet channel 43. The wafer 41 is made of silicon or of another suitable material using photolithographic processes in such a way as to define a pump chamber 44, an inlet valve 45 and an outlet valve 46 communicating with the pump chamber 44 via channels 47 and 48 respectively.

In this embodiment, a control element such as a piezoelectric disc 49 is placed directly on the silicon disc 41 in the zone which coincides with the pump chamber 44 so that, to obtain a pumping effect, it is this wafer 41 which is flexed to change the volume of the pump chamber. It is also desirable to provide a thin layer of silicon oxide 49a between the wafer 41 and the crystal 49 so as to insulate the corresponding electrode of the disc in respect of this wafer.

The wafer 42 only partially covers the wafer 41 and comprises an inlet opening 50 which opens into an annular compensation chamber 51 provided above the outlet valve 46. It will be noted that this valve is provided with a projection 52 making it possible to limit the amplitude of the membrane of this valve, the projection being able to bear against the lower face of the wafer 42 should the outlet pressure against the valve become excessive.

It will also be noted that the positions of the inlet and outlet valves 45 and 46 are reversed, the seat of the inlet valve being composed of the wafer 42 whereas the seat of the valve 46 is composed, as in the other embodiments, of the wafer 40. This arrangement has no special influence on the working of the pump.

Figure 11:
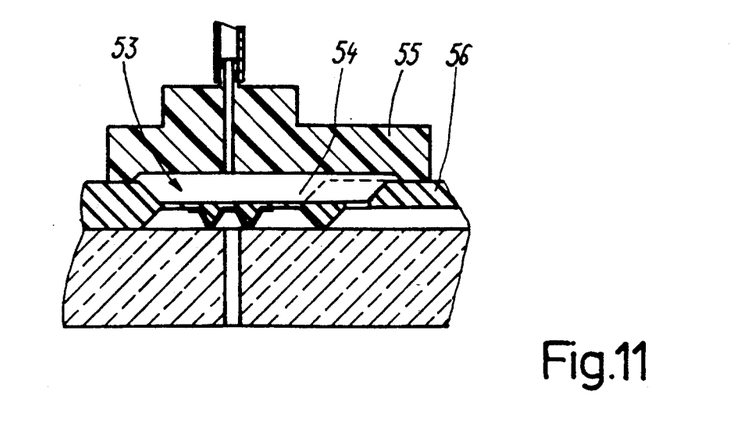
FIG. 11 shows a partial sectional view of a fifth embodiment of the invention.
Figure 12:
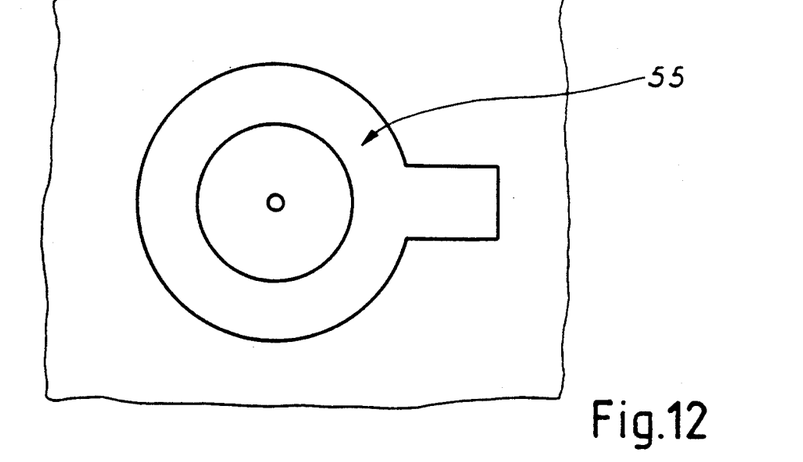
FIG. 12 is a partial plan view of the micropump shown in FIG. 11.

FIG. 11 shows another embodiment of the invention in which a chamber 54 above the outlet valve 53 is closed by a connection organ 55 made for example of plastic and bonded to the silicon wafer 56. The chamber 54 which, in effect, communicates with the inlet of the pump is totally insulated from the outer atmosphere. An advantage of this construction is that there is no need to use a special closing wafer.

As in the case of the pump of FIGS. 8–10 (channel 57) and in that of FIG. 11 (chamber 54), the outlet valves are connected to the pump inlet so as to guard against overpressure.

Figure 13:
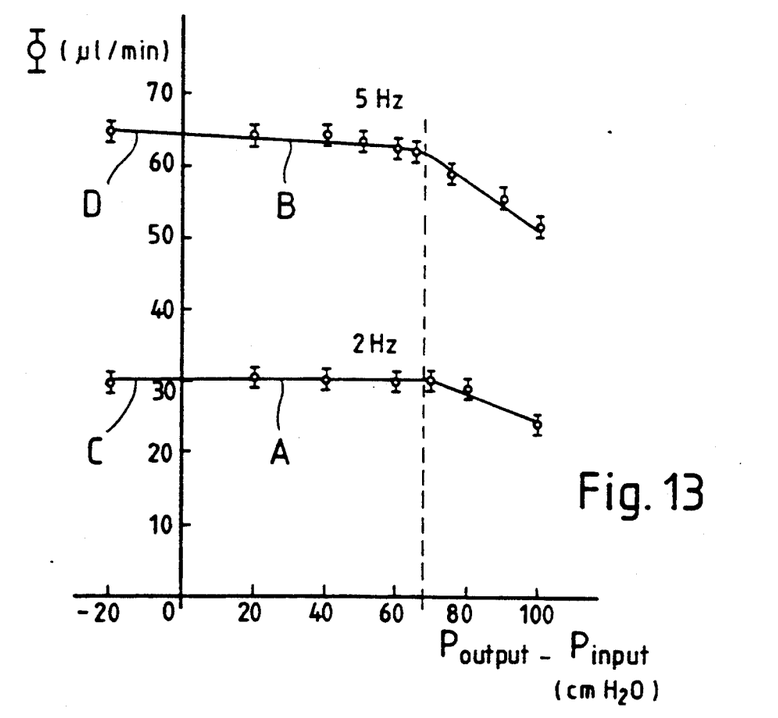
FIG. 13 is a graph showing the characteristics of the output as a function of the pressure measured in a micropump designed according to the invention where the inlet pressure equals zero.

The mode of operation of the micropump of the invention will now be examined with particular reference to the diagram of FIG. 13 which shows output as a function of pressure in the outlet channel.

It will be noted that the operation is the same in all the above described embodiments. For purposes of simplification the following description therefore relates only to the embodiment of FIGS. 1 and 2.

When no electric voltage is applied to the piezoelectric disc 13, the inlet valves 16 and outlet valves 18 are in the closed position. When an electric voltage is applied, the piezoelectric disc 13 flexes, causing the wafer 12 to bend towards the inside. The pressure in the pump chamber 15 therefore rises, actuating the opening of the outlet valve 18 as soon as the force acting on the membrane as a result of the pressure in the chamber 15 is greater than the difference between the force created by the pretension of the valve 18, ensured by the layer of silicon oxide 17 and the force resulting from the pressure in the outlet channel 3. The fluid contained in the pump chamber is thus driven towards the outlet channel 3 by displacement of the flexible zone of the wafer 12. During this phase, the inlet valve 16 is kept closed by the pressure prevailing in the pump chamber 15. The fluid runs without encountering noteworthy resistance so that the pump chamber 15 then communicates directly with the outlet channel 3.

In contrast, when the electrical voltage is cancelled, the piezoelectric disc 13 resumes its initial shape or is flexed in the other direction so that the pressure in the pump chamber 15 falls. This causes the outlet valve 18 to close as soon as the force induced by the pressure in the pump chamber 15 is lower than the difference between the force created by the pretension of the valve and the force due to the pressure in the outlet channel 3. The inlet valve 16 opens as soon as the sum of the force due to the pressure in the pump chamber and of the force created by the pretension of the valve 16 is lower than the force due to the pressure in the inlet channel 2. There is then aspiration of the fluid in the pump chamber 15 via the inlet channel 2 as a result of displacement of the flexible zone of the wafer 12.

By choosing a large ratio between the diameter of the membrane of the outlet valve 18 and its seat, the pressure in the outlet channel 3 has little influence on the pressure in the pump chamber needed to open the outlet valve. As a result, by carefully choosing this ratio as well as the control frequency of the piezoelectric disc, it is possible to ensure that the outlet pressure has only very little influence on the outlet output. It is thus possible to determine the outlet output/pressure curves such as those shown in FIG. 13. In this figure the curve A was obtained by applying a voltage at 2 Hz to the piezoelectric disc of a micropump according to FIGS. 3 to 5 having approximately the dimensions stated hereinabove, the outlet output remaining virtually constant at a value of 30 $\mu$l/min (most favourable choice). If one controls the piezoelectric disc with a voltage at 5 Hz, this outlet is brought to about 64 $\mu$l/min. Thus, as can be seen from the graphs of FIG. 13, the choice of a given pretension on the membrane of the outlet valve keeps the output constant at the values shown whereas the outlet pressure can vary from 0 to 70 cm $H_2O$. In addition, the graphs show that the output remains constant even for the negative values of the difference between the outlet pressure and the inlet pressure (parts C and D respectively of the graphs). This situation can, for example, arise when there is overpressure at the pump inlet.

It will be noted that the micropump, regardless of the embodiment described hereinabove, is compact and simple presents little resistance to flow and makes it possible to determine with very good approximation a constant output as a function of the outlet pressure.

In all the embodiments, except those of FIGS. 1 and 2, the pump was designed to guard against overpressure since the inlet of the pump communicates with a chamber situated above the outlet valve. Consequently, if such overpressure occurs, it acts on the outlet valve in the direction of closure, thereby insulating the outlet channel from the pump chamber. This property of the pump can be important when the pump is worn by a patient who also wears a flexible reservoir. If the latter compresses the reservoir (for example by knocking it against an obstacle) the overpressure in the pump aspiration does not cause any output on the outlet side thereof.

In addition, due to the communication between the compensation chamber and the pump inlet, variation in the inlet pressure has only very little influence on the outlet output in the normal operating range of the pump.

It should be noted that the communication can also be effected by a connection outside the pump. For example, the pump of FIGS. 1 and 2 could be provided with a tube connecting the inlet to the outlet.

Finally, FIG. 1 shows that it is possible to connect an operating control element to the silicon wafer for example in the form of a strain gauge 11A, the variation in the resistance of which could be measured to show that the pump is operating correctly or else the membrane on which the gauge is bonded has ruptured. One or several of these control elements may of course be provided in all the embodiments described.

What is claimed is:

1. A micropump comprising a first wafer, at least one second wafer adhered face to face to said first wafer to form a pump chamber, and actuator means for causing a periodic variation in the volume of said pump chamber, wherein said first wafer is made of a material capable of being machined using photolithographic technology and is machined in such a way as to define said pump chamber, a first valve of the check-valve type through which said pump chamber can selectively communicate with an inlet of the pump and a second valve of the membrane type through which said pump chamber can selectively communicate with an outlet of the pump, wherein said outlet communicates directly with an isolated volume of said pump chamber defined by an annular rib of said second valve in its closed position, wherein said annular rib of said second valve, said outlet of the pump and a channel through which said second valve communicates with the pump chamber are situated on the same side of said first wafer in such a way that the pressures prevailing respectively in said pump chamber and in said outlet act in the direction of opening said second valve, wherein said pump is without a valve of the check-valve type between said first and second valves such that said second valve is in continuous communication with said first valve via said pump chamber during the input phase of the pump and said pump chamber communicates directly with said outlet via said second valve in its open position during the output phase of the pump, and wherein said second valve is pretensioned to be normally closed such that pump output is substantially independent of outlet pressure over a predetermined pressure range.

2. A micropump according to claim 1, wherein the pump inlet communicates with a compensation chamber disposed above said second valve so as to close the latter under the influence of the pressure prevailing at said inlet.

3. A micropump according to claim 1, wherein a detector element, such as a strain gauge is fixed to said first wafer to monitor the correct working of the pump.

4. A micropump according to claim 3, wherein the pump inlet communicates with a compensation chamber disposed above said second valve so as to close the latter under the influence of the pressure prevailing at said inlet.

5. A micropump according to claim 1, wherein it comprises a third wafer covering said first wafer at least over part of its surface and delimiting therewith at least one chamber designed to form an active cavity of the pump.

6. A micropump according to claim 5, wherein the pump inlet communicates with a compensation chamber disposed above said second valve so as to close the latter under the influence of the pressure prevailing at said inlet.

7. A micropump according to claim 5, wherein said means provided for causing a periodic variation in the volume of the pump chamber comprises a piezoelectric disc fixed to said third wafer in a zone coinciding with said pump chamber.

8. A micropump according to claim 7, wherein the pump inlet communicates with a compensation chamber disposed above said second valve so as to close the latter under the influence of the pressure prevailing at said inlet.

9. A micropump according to claim 5, wherein said means provided for causing a periodic variation in the volume of the pump chamber comprise a piezoelectric disc, in that said pump chamber is delimited by said first and second wafers and in that said piezoelectric disc is fixed to said first wafer in an uncovered zone of the same coinciding with said pump chamber.

10. A micropump according to claim 9, wherein the pump inlet communicates with a compensation chamber disposed above said second valve so as to close the latter under the influence of the pressure prevailing at said inlet.

11. A micropump according to claim 5, wherein said third wafer is so designed as to also form at least one connection by which said actuator means can be connected to an external actuating circuit.

12. A micropump according to claim 11, wherein the pump inlet communicates with a compensation chamber disposed above said second valve so as to close the latter under the influence of the pressure prevailing at said inlet.

13. A micropump according to claim 1, wherein said first valve and/or said second valve comprises a membrane provided in the plan of said first wafer and in the center of which is provided an annular rib, wherein the top of said rib is designed to bear against another wafer serving as a seat for this valve, and wherein at least said rib is covered by an oxide layer inducing in the membrane a predetermined pretension so that the valve is normally closed.

14. A micropump according to claim 13, wherein the pump inlet communicates with a compensation chamber disposed above said second valve so as to close the latter under the influence of the pressure prevailing at said inlet.

15. A micropump according to claim 13, wherein the membrane of the second valve is at least partially covered by a layer of a material which creates shearing forces in the membrane thereby inducing additional pretension.

16. A micropump according to claim 15, wherein the pump inlet communicates with a compensation chamber disposed above said second valve so as to close the latter under the influence of the pressure prevailing at said inlet.

17. A micropump according to claim 13, wherein on the side opposite said rib, said membrane is provided with a projection extending towards another wafer of the pump and designed to limit the travel of the membrane in the event that this is subjected to an excess pressure.

18. A micropump according to claim 17, wherein the pump inlet communicates with a compensation chamber disposed above said second valve so as to close the latter under the influence of the pressure prevailing at said inlet.

19. A micropump according to claim 13, wherein the rib provided respectively on the membrane of said first valve and on the membrane of said second valve are disposed on opposite faces of these membranes.

20. A micropump according to claim 19, wherein the pump inlet communicates with a compensation chamber disposed above said second valve so as to close the latter under the influence of the pressure prevailing at said inlet.

* * * * *